(12) United States Patent
Cecchi

(10) Patent No.: US 7,985,579 B2
(45) Date of Patent: Jul. 26, 2011

(54) SPECIMEN CULTURING ASSEMBLY SUITABLE FOR USE IN IN-VITRO FERTILIZATION AND IN OTHER CELL CULTURING PROCEDURES

(75) Inventor: Michael D. Cecchi, Madison, CT (US)

(73) Assignee: GENX International, Inc., Guilford, CT (US)

( * ) Notice: Subject to any disclaimer, the term of this patent is extended or adjusted under 35 U.S.C. 154(b) by 840 days.

(21) Appl. No.: 11/985,845

(22) Filed: Nov. 19, 2007

(65) Prior Publication Data

US 2009/0130750 A1    May 21, 2009

(51) Int. Cl.
*C12M 1/34* (2006.01)
*C12M 3/00* (2006.01)
*C12M 1/22* (2006.01)

(52) U.S. Cl. .................. 435/288.4; 435/305.2

(58) Field of Classification Search ............ 435/288.4, 435/305.2
See application file for complete search history.

(56) References Cited

U.S. PATENT DOCUMENTS 5,609,827 A * 3/1997 Russell et al. ............ 422/102
2008/0003672 A1 * 1/2008 Cecchi et al. ............ 435/305.2

* cited by examiner

*Primary Examiner* — Walter D Griffin
*Assistant Examiner* — Lydia Edwards
(74) *Attorney, Agent, or Firm* — William W. Jones

(57) ABSTRACT

An assembly is disclosed that is to be used for the culturing of specimens such as embryos and gametes for use in in vitro fertilization. The assembly includes an annular ring which is affixed to the stage of an optical viewing instrument, such as a microscope. The viewing instrument is focused on a point which lies inside of the ring at a predetermined distance from the center of the ring. Circular specimen dishes having a plurality of specimen wells in which the specimens in question are cultured or grown is removably positioned inside of the ring. The specimen wells have bottom walls which are configured so as to ensure that the specimens in the wells will gravitate to the same predetermined position in each of the wells. That position coincides with the focus point of the viewing instrument. When the specimen culturing dishes are placed inside of the ring, they can be rotated inside of the ring to bring the specimens in each well sequentially into the focus point of the viewing instrument whereby the specimens in each dish can be quickly and accurately monitored for growth and development. Other devices are disclosed which enable the rotation of the dish and proper alignment of the specimens in each well with the focus point of the viewing instrument. The assembly can be used for a wide range of specimen culturing. Typical specimens include animal and human cells, tissues, stem cells, embryos, oocytes, immature oocytes, sperm precursor cells, embryonic cells, blastocysts, and spermatozoa.

14 Claims, 3 Drawing Sheets

SPECIMEN CULTURING ASSEMBLY SUITABLE FOR USE IN IN-VITRO FERTILIZATION AND IN OTHER CELL CULTURING PROCEDURES

TECHNICAL FIELD

This invention relates to an assembly that is to be used for the culturing of specimens such as embryos and gametes for use in ingg vitro fertilization. The assembly includes at least two components, one of which has a plurality of specimen wells in which the specimens in question are cultured or grown. The specimens may constitute other mammalian or plant cells. The assembly can be used for a wide range of specimen culturing. Typical specimens include animal and human cells, tissues, stem cells, embryos, oocytes, immature oocytes, sperm precursor cells, embryonic cells, blastocysts, and spermatozoa.

BACKGROUND ART

Conventional Petrie dishes used for procedures such as observation, growth, expansion, biopsy and manipulation of mammalian cells are not unique and are mostly generic. The user usually has to add droplets or media pools to the flat surface of the dish and then use it for the particular purpose. The media pools are thus randomly placed in the Petrie dish, and thus the technician must spend additional time locating the various media pools and observing the specimens in the individual media pools. The time spent can be minutes to tens of minutes. The standard Petrie dish thus complicates the process of monitoring specimen growth and development, and complicates the ability to tell which specimen is which.

One problem with using generic Petri dishes in specimen procedures is that they do not have unique dish configurations which enhance their utility in such procedures. Another problem with the current dishes is that they require the user to use micro drops of a specimen medium solution on the surface of the dish. Some dishes may create surface tension problems with the specimen medium solution. This can result in the micro drops collapsing and the media solution that the sample is in then becomes compromised by an overlain layer of oil. The reverse may happen too and the droplets may not adhere well to the bottom of the dish causing them to move in the dish.

It would be highly desirable to provide a specimen treatment dish assembly that will inherently locate the specimen being treated in a definite predetermined location in the dish and retain the specimen in that definite location. It would be further desirable to provide a specimen treatment dish assembly which does not require movement of the optics, such as a microscope, to observe and log the changes in the several specimens being treated in the dish.

DISCLOSURE OF THE INVENTION

This invention relates to an improved container or dish assembly for treating biological specimens such as ova, sperm, embryos, skin cells, and the like, which dish can be used in combination with an optical viewing instrument whereby the specimens can be optically observed during different stages of the treatment protocol. The dish assembly includes at least two components, one of which is held stationary on the optical instrument viewing stage, and another of which contains specimen wells and is movable on the optical instrument viewing stage. Preferably, the movable component is arranged so as to rotate inside of the stationary component. The annular outer component is stationary on the viewing stage, and the inner circular component rotates within the annular outer component.

The inner component will be provided with wells which contain specimens and/or reagents that are used in the specimen treatment procedures. The assembly will have an axis of rotation on the optical instrument stage about which any rotatable component will rotate. The wells in the inner component will be equiangularly spaced about the axis of rotation, so that the wells will be a known distance apart from each other. The wells can be rectilinear in configuration or circular. The wells will have bottom surfaces what are conical or pyramidal in shape so that anything in the wells will gravitate to a predetermined location in the wells. This predetermined location is located a predetermined radial distance from the axis of rotation.

The optical system is fixed relative to the stage in a position that places the field of view of the optical system inside of the outer annular member and wherein that field of view position is located at the same predetermined distance from the center of the assembly. Thus, the optical system is positioned to sequentially view specimens in each well in the rotatable dish component. The monitoring instrument can be provided with a number of preset focus planes, or can be manually focused if so desired.

BRIEF DESCRIPTION OF THE DRAWINGS

These and other objects and advantages of the invention will become more readily apparent from the following detailed description of several embodiments of the invention when taken in conjunction with the accompanying drawings in which.

DETAILED DESCRIPTION OF SPECIFIC EMBODIMENTS OF THE INVENTION

Figure 1:
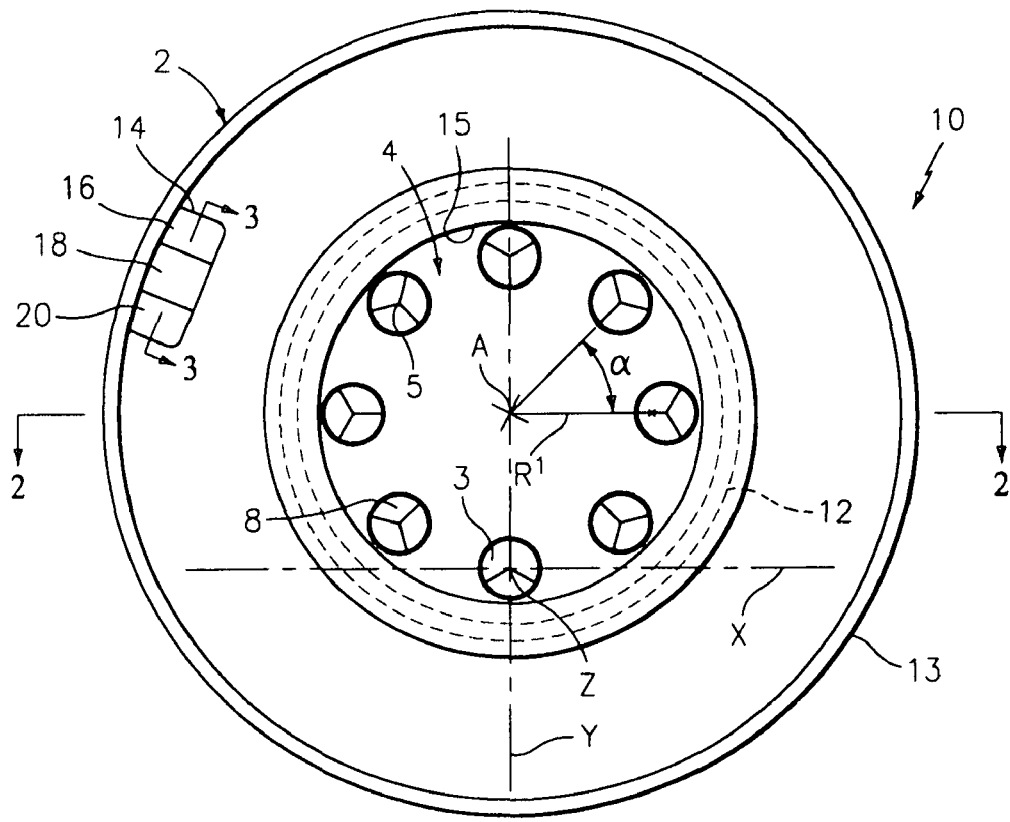
FIG. 1 is a top plan view of a first embodiment of a specimen dish assembly formed in accordance with this invention.
Figure 2:
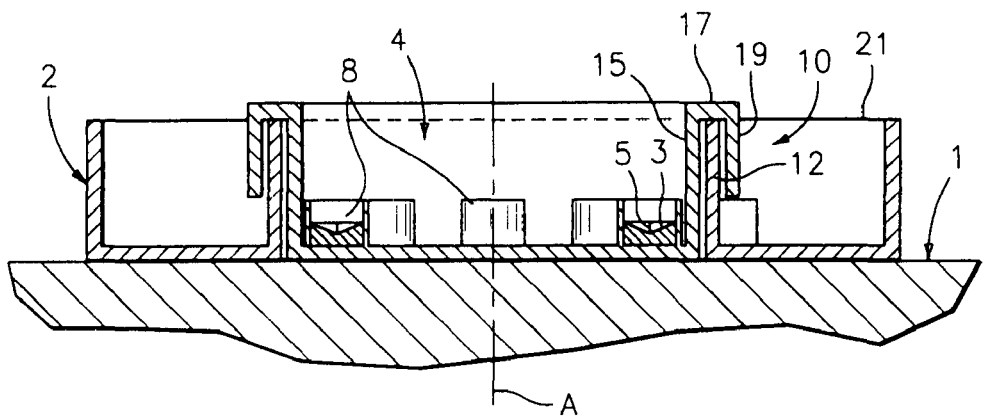
FIG. 2 is a sectional view of the dish assembly taken along line 2-2 of FIG. 1.

Referring now to FIGS. 1 and 2, FIG. 1 is a top plan view of a specimen handling dish assembly identified generally by the numeral 10 formed in accordance with this invention. The dish assembly includes an outer annular component 2 and an inner circular component 4. The outer component 2 is fixed to a stage 1 of an optical viewing instrument such as a microscope (not shown). The inner component 4 includes wells 8 are radially spaced apart from the axis A of the assembly 10 by a distance $R^1$. The bottom surfaces 3 of the wells 8 are formed as inverted pyramids with the central deepest point 5 in the wells 8 are disposed on the circumference defined by the radial distance $R^1$. The microscope used in connection with the system is positioned at the position defined by the lines of alignment X and Y at the location Z which is located on the circumference defined by $R^1$.

Thus when a specimen monitoring optical device is properly spaced apart from the axis A, it will be zeroed in on the center 5 of each of the wells 8. This ensures that an embryo, or other specimen to be treated in the assembly which migrates to the center 5 of any well 8 containing that specimen can be easily located by a microscope.

The outer component 2 may include an inner vertical wall 12 and an outer vertical wall 13. The inner component 4 has an outer vertical wall 15 which overlies the inner vertical wall 12, as shown in detail in FIG. 2, which allows the inner dish component 4 to be rotated in the outer component 2 about the axis A. The outer component 2 may include an optical device focusing section which has a plurality of focusing planes that can be used in a manner described hereinafter, to focus an optical monitoring device, such as a microscope.

Figure 3:
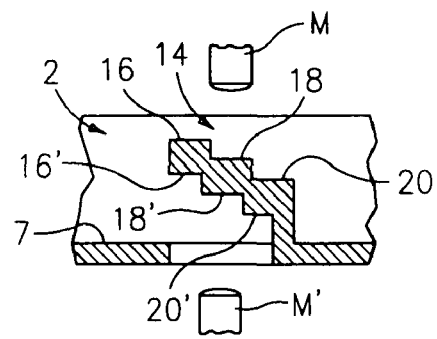
FIG. 3 is a sectional view of a portion of the dish assembly taken along line 3-3 of FIG. 1.
Figure 4:
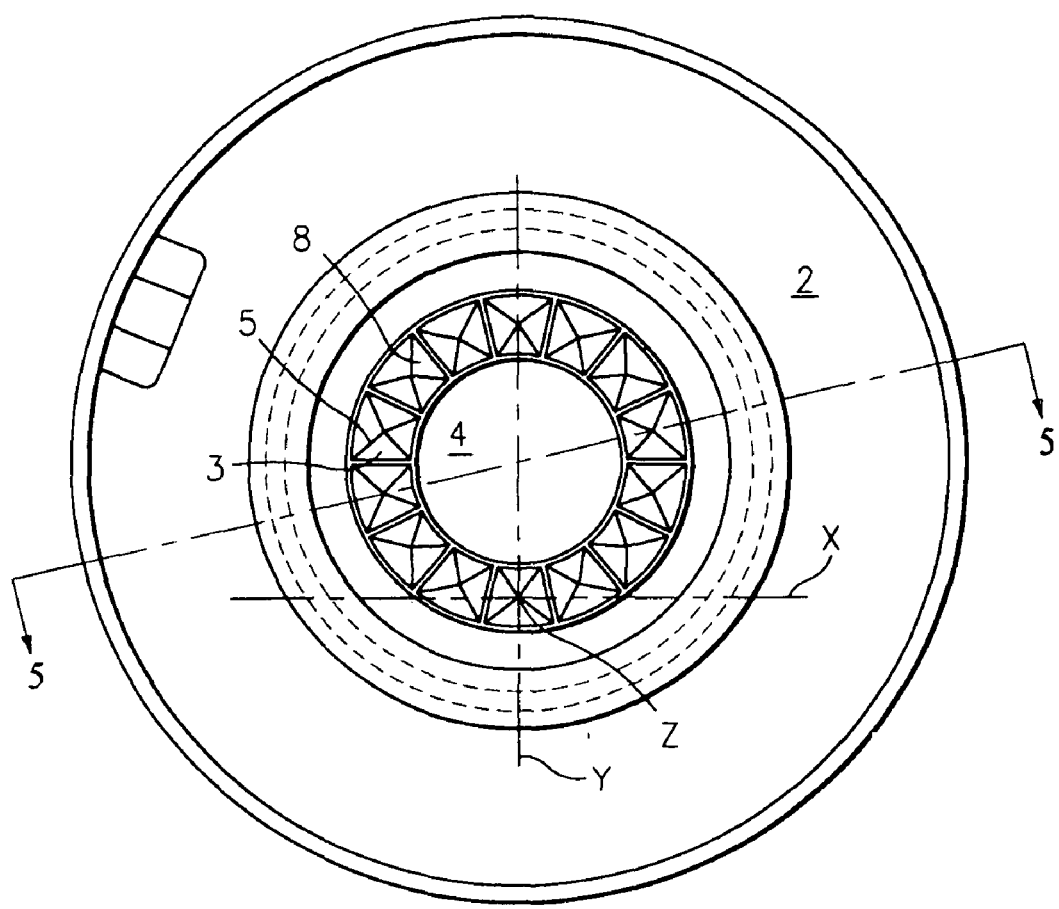
FIG. 4 is a plan view of a second embodiment of a specimen dish assembly formed in accordance with this invention.
Figure 5:
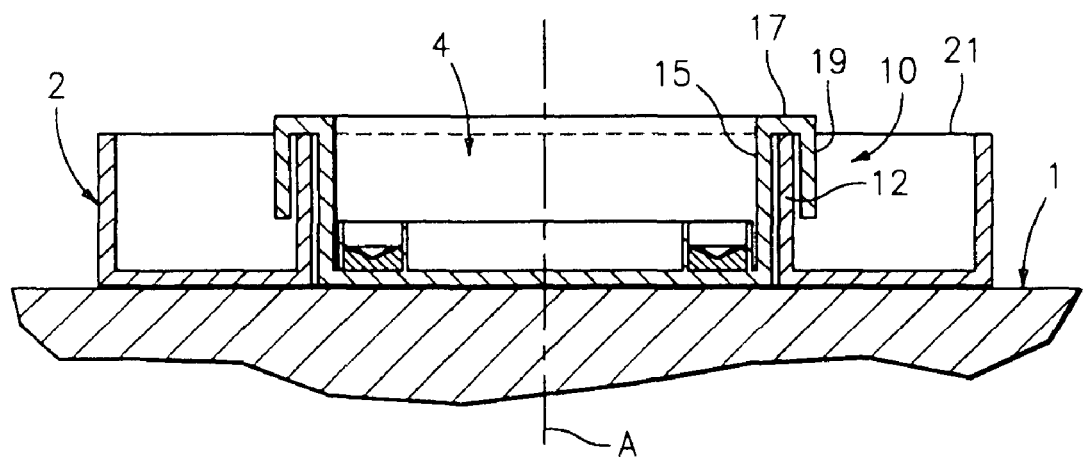
FIG. 5 is a sectional view of the dish assembly of FIG. 4 taken along line 5-5 of FIG. 4.

Referring now to FIG. 3, details of the optical focusing section 14 included in the assembly 10 are disclosed. The focusing section 14 is positioned on the bottom surface 7 of the outer component 2 of the assembly 10, and it includes a plurality of horizontal planar upper and lower surfaces 16, 16', 18, 18' and 20, 20'. These surfaces can be used to pre-focus an optical viewing instrument, such as a microscope M, M', so as to selectively be pre-focused in on the bottom surface of the wells 8. The surfaces 16, 16', 18,18' and 20, 20' of the focusing section 14 will be made optically distinguishable one from another. Thus the optical instrument M, M' can be positioned over or under the section 14, and will use whichever of the surfaces 16, 16', 18, 18', or 20, 20' coincide with the bottom surfaces 5, or other surface depths such as the side walls of the wells 8 to store focusing information for later use in observing specimens that are positioned in the wells 8.

The dish assembly 10 is used in the following manner. The outer component 2 is fixed to the microscope stage 1 as noted above and the microscope is positioned on the X, Y, Z optical axis shown in the drawings. A dish 4 containing a culturing media and an embryo in each of the wells 8 is inserted into the outer member 2. It will be noted that the dish 4 shown in FIG. 1, for example, contains eight wells 8. Typically eight embryos will be removed from a donor and cultured for about five days before being reimplanted. If more than eight embryos are taken from a donor, then more than one culturing dish will be used to treat the embryos. The number of embryos which are reimplanted is typically one to three. This being the case, the embryos which are being cultured are monitored periodically to see which of the embryos appear to be the most viable for reimplantation. The eight embryos will be placed in the wells 8 of the dish 4 and the wells 8 can be numbered or lettered sequentially so that each well 8 will be recorded as containing a particular embryo. This being the case, one monitoring the development of the individual embryos in any dish 4 need merely place the dish 4 in side of the member 2 and rotate the dish 4 until one of the wells 8 is positioned in the field of view of the microscope. The number or letter of that well 8 is recorded as is the status of the embryo in that well. The dish 4 is then rotated until the next well 8 comes into view, and the status of the embryo in that next well is recorded along with the number or letter of that well. The aforesaid procedure is repeated until all of the embryos in the wells 8 have been viewed and their status upgraded. After that procedure which will take about one or two minutes to perform, the dish 4 is removed and another dish 4 is placed in the member 2 so that another review of each of the embryos in the subsequent dish 4 can be performed and recorded. It will be appreciated that the number of embryos that can be monitored in a given amount of time is greatly enhanced through the use of the assembly of this invention since the location of each of the embryos is fixed and known and one does not have to spend considerable amounts of time searching for the embryos in the culturing dish.

FIGS. 4-7 illustrate further embodiments of the invention which can be used in the manner described above. In the embodiment shown in FIGS. 4 and 5, the specimen wells 8 are relatively rectilinear in configuration and share common walls with adjacent wells. This configuration will allow the dish 4 to receive more specimens and may be a configuration which may be more useful in the freezing and thawing of oocytes and sperm, for example. The focus point Z of the microscope will be at the lowest point 5 in the bottom wall 3 of each of the wells 8 as the dish 4 is rotated inside of the stationary outer ring-shaped member 2.

Figure 6:
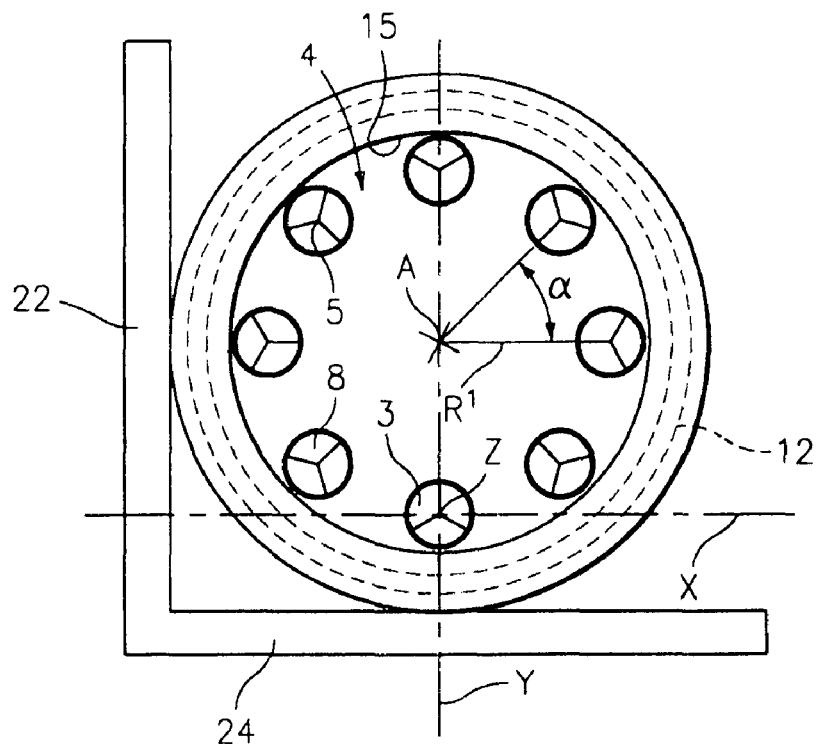
FIG. 6 is a plan view of yet another embodiment of a specimen dish assembly formed in accordance with this invention.

In the embodiment shown in FIG. 6, the dish 4 is pressed against perpendicular stops 22 and 24 which are fixed to the microscope stage. In this manner the focus point Z of the microscope will remain on the lowest point 5 in the bottom wall 3 of each well 8 as the dish 4 is rotated against the stops 22 and 24.

Figure 7:
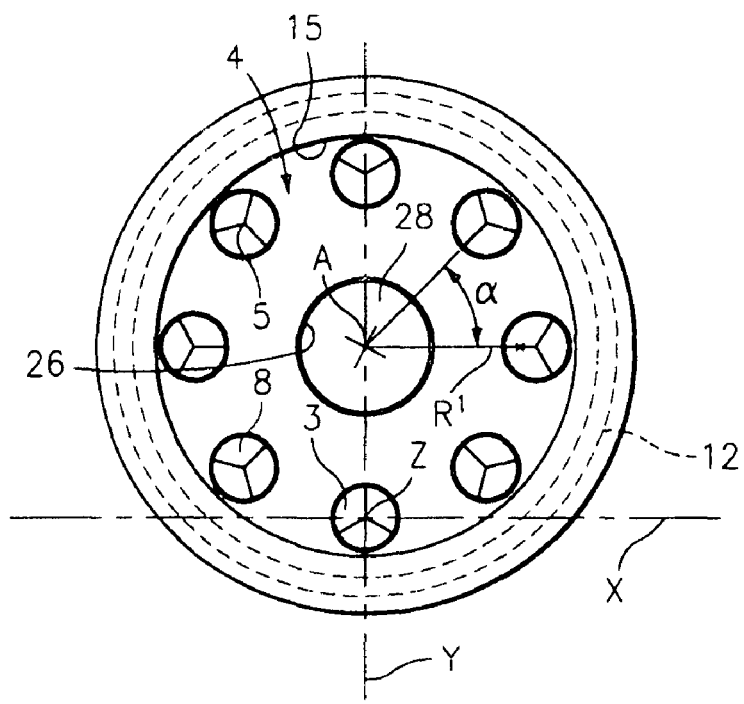
FIG. 7 is a plan view of still another embodiment of a specimen dish assembly formed in accordance with this invention.

In the embodiment shown in FIG. 7, the dish 4 includes a central circular opening 26 which receives a post 28 that is fixed to the microscope stage. The Z axis of the microscope focus point is centered on the lowest point 5 is the bottom wall 3 of the wells 8, so that when the dish 4 is rotated around the post 28, each well 8 will be properly positioned in the focus point of the microscope.

It will be appreciated that the dish assembly of this invention can be used in procedures which include growing, fertilization, observation, micro manipulation, biopsies, and freezing and thawing of specimens. The specimens that may be used in the procedures include oocytes, embryos, sperm, stem cells, ovarian tissue, and bacteria, to name a few. The dish of this invention and the system incorporating the dish greatly reduces the time needed to perform any procedure which involves placing specimens in wells and treating the specimens in the wells because the wells are all strategically located in the dish so that the specimens in the wells can be quickly and easily monitored during the procedure in question.

While the invention has been described with respect to preferred embodiments, those skilled in the art will readily appreciate that various changes and/or modifications can be made to the invention without departing from the spirit or scope of the invention as defined by the appended claims.

What is claimed is:

1. An assembly for use in culturing biological specimens such as embryos, gametes and zygotes for use in in vitro fertilization, said assembly comprising:
   a) a first component which contains a pluralty of wells for receiving biological specimens to be cultured;
   b) at least a second component which engages said first component;
   c) a specimen monitoring instrument for monitoring specimens which are disposed in said wells, said specimen monitoring instrument providing an optical axis which is fixed relative to said first and second components; and
   d) said first component being selectively movable relative to said second component so that individual specimens disposed in said wells in said first component will be brought into alignment with said optical axis so that development of the individual specimens can be monitored during a culturing process.

2. The assembly of claim 1 wherein said second component is spatially fixed relative to said optical axis.

3. The assembly of claim 1 wherein said first component is rotatably mounted relative to said second component.

4. The assembly of claim 3 wherein said second component comprises two fixed stops and wherein said first component includes an outer surface which slidably engages said fixed stops whereby said first component can rotate by sliding over said fixed stops.

5. The assembly of claim 1 wherein said second component is annular in configuration and includes an axial central opening and wherein said first component is circular in configuration and is mounted in said axial central opening, said first component being rotatable in said axial central opening so as to selectively move said specimens in said wells into sequenced alignment with said optical axis.

6. The assembly of claim 1 wherein said first component is annular in configuration and includes an axial central opening and wherein said second component is circular in configuration and is disposed in said central opening, said first component being rotatable about said second component so as to selectively move said specimens in said wells into sequenced alignment with said optical axis.

7. The assembly of claim 1 wherein said bottom surfaces in each of said wells are in the form of inverted cones or pyramids so as to form a nadir area in each of said wells into which nadir areas said specimens will settle after being placed in said wells.

8. The assembly of claim 7 wherein said nadir areas are sequentially brought into alignment with said optical axis by movement of said first component relative to said second component during specimen examination.

9. The assembly of claim 7 wherein said nadir areas are each offset from an axis of rotation of said first component by the same distance and are circumferentially distributed about said axis of rotation.

10. The assembly of claim 1 wherein said optical axis is offset from said axis of rotation by said same distance.

11. The assembly of claim 1 wherein one of said components includes an optical device focussing section having a plurality of optically distinguishable surfaces which are disposed at different depths in said one of said components and which different depths coincide with different specimen-containing parts of said wells and which enable an optical device to be prefocussed on one or more predetermined areas in said wells.

12. The assembly of claim 11 wherein said optically distinguishable surfaces are formed as steps in said focussing section.

13. The assembly of claim 12 wherein said steps face upwardly on said one of said components.

14. The assembly of claim 12 wherein said steps face downwardly on said one of said components.

* * * * *